US012729345B2

(12) United States Patent
Arjah et al.

(10) Patent No.: US 12,729,345 B2
(45) Date of Patent: Sep. 8, 2026

(54) PROCESS AND CATALYST FOR CONVERTING NATURAL GASOLINE TO LIGHT OLEFINS

(71) Applicants: Saudi Arabian Oil Company, Dhahran (SA); King Fahd University of Petroleum and Minerals, Dhahran (SA)

(72) Inventors: Abeer S. Arjah, Dhahran (SA); Qi Xu, Dhahran (SA); Mohammed AlAmer, Dammam (SA); Mohammad Mozahar Hossain, Dhahran (SA); Sagir Adamu, Dhahran (SA); Akolade Idris Bakare, Dhahran (SA)

(73) Assignees: Saudi Arabian Oil Company, Dhahran (SA); King Fahd University of Petroleum and Minerals, Dhahran (SA)

( * ) Notice: Subject to any disclaimer, the term of this patent is extended or adjusted under 35 U.S.C. 154(b) by 211 days.

(21) Appl. No.: 18/672,781

(22) Filed: May 23, 2024

(65) Prior Publication Data

US 2025/0361454 A1 Nov. 27, 2025

(51) Int. Cl.
*C10G 57/00* (2006.01)
*B01J 29/48* (2006.01)
(Continued)

(52) U.S. Cl.
CPC .............. *C10G 57/00* (2013.01); *B01J 29/48* (2013.01); *B01J 29/7057* (2013.01); *B01J 29/90* (2013.01);
(Continued)

(58) Field of Classification Search
CPC ........ B01J 29/48; B01J 29/7057; B01J 29/90; B01J 37/0201; B01J 37/30; B01J 38/12;
(Continued)

(56) References Cited

U.S. PATENT DOCUMENTS 7,235,706 B2 * 6/2007 Iezzi .......................... B01J 8/26 585/654
2010/0022811 A1 1/2010 Sousa Aguiar et al.
2017/0313636 A1 * 11/2017 Wang .................... C07C 5/3335

FOREIGN PATENT DOCUMENTS

| CN | 102690683 B | 1/2015 |
|---|---|---|
| WO | 2018156431 A1 | 8/2018 |
| WO | 2024073336 A1 | 4/2024 |

OTHER PUBLICATIONS

Notification of Transmittal of the International Search Report and Written Opinion of the International Searching Authority, or the Declaration dated Aug. 14, 2025 pertaining to International application No. PCT/US2025/029978 filed May 19, 2025, pp. 1-15.
Ghazimoradi, Maryam et al. "Effect of simultaneous dealumination and metal incorporation of zeolite ZSM-5 on the catalytic performance in HTO process", Microporous and Mesoporous Materials, Mar. 1, 2023, pp. 1-11, 112486, vol. 351, Amsterdam, NL.
(Continued)

*Primary Examiner* — James C Goloboy
(74) *Attorney, Agent, or Firm* — Dinsmore & Shohl LLP

(57) ABSTRACT

The present disclosure is directed to methods of and catalyst systems for converting natural gasoline liquid (NGL) feed to light olefins. The catalyst systems are capable of catalyzing both catalytic cracking and dehydrogenation processes. The catalyst systems include a metal-substituted zeolite comprising a MFI-type and/or a BEA-type framework comprising 0.5 wt. % to 30 wt. % cerium and/or vanadium atoms based on a total weight of the metal-substituted zeolite. The methods include contacting the NGL feed with the catalyst system in a reactor system, thereby converting a portion of the NGL feed to the light olefins and yielding a product stream comprising the light olefins.

17 Claims, 4 Drawing Sheets

(51) Int. Cl.
*B01J 29/70* (2006.01)
*B01J 29/90* (2006.01)
*B01J 37/02* (2006.01)
*B01J 37/30* (2006.01)
*B01J 38/12* (2006.01)
*C07C 5/54* (2006.01)
*C10G 11/05* (2006.01)
*C10G 11/18* (2006.01)

(52) U.S. Cl.
CPC .......... *B01J 37/0201* (2013.01); *B01J 37/30* (2013.01); *B01J 38/12* (2013.01); *C07C 5/54* (2013.01); *C10G 11/05* (2013.01); *C10G 11/18* (2013.01); *B01J 2229/183* (2013.01); *C07C 2529/48* (2013.01); *C10G 2400/20* (2013.01)

(58) Field of Classification Search
CPC .. B01J 2229/183; C07C 5/54; C07C 2529/48; C10G 11/05; C10G 11/18; C10G 57/00; C10G 2400/20
See application file for complete search history.

(56) References Cited

OTHER PUBLICATIONS

Hu, Xiaoyan et al. “Different influences of V2O5/Al2O3 introduction on initial conversion of n-heptane over fresh and equilibrium ZSM-5 catalyst”, Chemical Engineering Research and Design, Feb. 1, 2015, pp. 105-111, vol. 94, Amsterdam, NL.
Almuqati, Naif S et al. “Catalytic production of light Olefins: Perspective and prospective”, Fuel, IPC Sience and Technology Press, Mar. 1, 2024, pp. 1-27, 131270, vol. 366, Guildford, GB.
Naicker, T. et al. “Hexane activation over vanadium modified zeolite ZSM-5”, Journal of Porous Materials, Nov. 7, 2012, pp. 763-775, vol. 20, No. 4, New York.
Amusa et al., “High-performance VOx on SrO-yAl2O3 catalyst for oxidative cracking of n-hexane to light olefins under anaerobic environment”, Journal of Industrial and Engineering Chemistry, vol. 89, pp. 339-350, 2020.
Amusa et al., “Kinetics of Oxidative Cracking of n-Hexane to Light Olefins using Lattice Oxygen of a VOx/SrO-yAl2O3 Catalyst”, Asian Chemical Editorial Society, vol. 16, pp. 1-16, 2021.

* cited by examiner

PROCESS AND CATALYST FOR CONVERTING NATURAL GASOLINE TO LIGHT OLEFINS

FIELD

The present application is related to processes of producing light olefins, and in particular, to process of producing light olefins by converting natural gasoline liquid (NGL).

BACKGROUND

Light olefins are important building blocks for a wide range of valuable products such as plastics and petrochemicals. For example, ethylene is the primary feedstock for producing valuable polyethylene and iso-butylene is the feedstock for producing butyl rubber.

Typically, light olefins are produced by steam cracking processes, which convert alkane fractions to light olefins. However, steam cracking processes produce primarily ethylene, and the yields of more valuable propylene and butylene are generally low. Further, steam cracking processes are generally operated at a temperature above 800° C. and are therefore energy-intensive.

Efforts have been made to develop alternative processes to selectively produce propylene and, in particular, butylene. Dehydrogenation has been considered as a promising route to selectively produce butylene. During a dehydrogenation process, olefins are formed by the removal of hydrogen atoms, instead of cleaving the carbon-carbon single bonds, at an operating temperature much lower (<600° C.) than the steam cracking process. However, the yield of selected olefin depends on the composition of the hydrocarbon feedstock. Appropriate hydrocarbon feedstock (e.g. propane, n-butane, or iso-butane) is required in order to produce selected olefins such as propylene or butenes.

Accordingly, a need exists for a process of selectively producing light olefins with a high yield that is not limited to the feedstock composition and that is energy-efficient.

SUMMARY

Embodiments of the present disclosure meet this need by utilizing catalyst systems that are capable of catalyzing both catalytic cracking and dehydrogenation processes to selectively produce light olefins using natural gasoline liquid (NGL) as feedstock. In particular, the catalyst systems disclosed herein comprise a metal-substituted zeolite comprising a MFI-type and/or a BEA-type framework, and the metal-substituted zeolite may further comprise cerium and/or vanadium atoms. As discussed herein, the catalyst systems are capable of converting natural gasoline liquid to valuable light olefins with a selectivity of from 30 wt. % to 70 wt. % and a relatively high selectivity towards butenes of from 20 wt. % to 80 wt. % among the light olefins.

Embodiments of this disclosure are directed to methods of converting an NGL feed to light olefins. The methods may comprise contacting the NGL feed comprising alkanes with a catalyst system that catalyzes catalytic cracking and dehydrogenation in a reactor system, thereby converting a portion of the NGL feed to light olefins and yielding a product stream comprising the light olefins, wherein the catalyst system comprises a metal-substituted zeolite comprising a MFI-type and/or a BEA-type framework comprising 0.5 wt. % to 30 wt. % cerium and/or vanadium atoms based on the total weight of the catalyst system.

Additional features and advantages will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE SEVERAL VIEWS OF THE DRAWINGS

The following detailed description of specific embodiments of the present disclosure can be best understood when read in conjunction with the following drawings in which.

DETAILED DESCRIPTION

Figure 1:
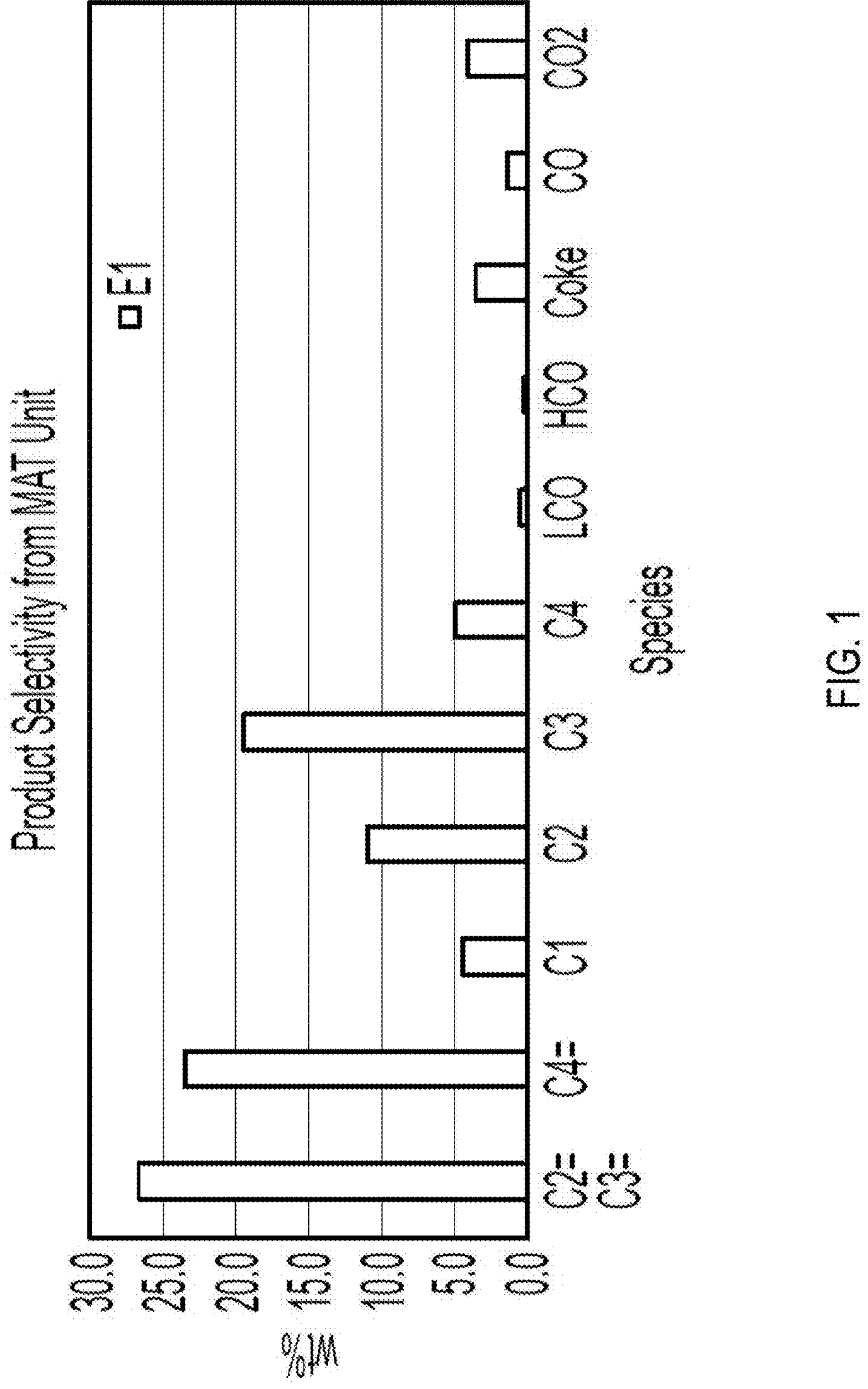
FIG. 1 illustrates product distribution of converting NGL feed to light olefins in the MAT unit using a catalyst system comprising a vanadium oxides ($VO_x$)-impregnated ZSM-5 zeolite ($VO_x$/ZSM5)

NGL is rich in straight and branched paraffin containing five or six carbons and therefore is a promising alternative source for producing light olefins including ethylene, propylene, and butenes. However, it is generally known that dehydrogenation of alkanes are often accompanied with side reactions competing with the alkane-to-alkene conversion resulting in a reduced selectivity and a reduced yield of alkenes. Some side reactions are equilibrium-dependent or temperature-dependent and particularly difficult to control in the conversion of a feed stream comprising a mixture of hydrocarbons, such as the NGL feed.

Nonetheless, as disclosed herein, a combination of catalytic cracking and dehydrogenation processes provides a viable route to efficiently convert natural gasoline liquid to light olefins. The combined process is termed as "catalytic oxidative cracking." References will now be made in detail to embodiments of catalyst systems that catalyzes catalytic oxidative cracking.

The catalyst systems disclosed herein are rich in lattice oxygen that, without being bound by any particular theory, are capable of activating an alkane-to-alkene conversion substantially in the absence of a gaseous oxidant. As used herein, "gaseous oxidant" refers to an oxidizing gas comprising at least one oxygen atom. Example gaseous oxidants include oxygen, ozone, carbon dioxide, nitrogen dioxide, and dinitrogen oxide. For example, and according to embodiments, the catalyst systems may comprise a metal-substituted zeolite comprising a MFI-type and/or a BEA-type framework. In one or more embodiments, the metal-substitute zeolite may have a silica-to-alumina molar ratio of from 10 to 500, such as from 10 to 250, from 10 to 100, from 10 to 50, from 20 to 500, from 20 to 250, from 20 to 100, from 20 to 50, from 50 to 500, from 50 to 250, from 50 to 100, from 100 to 500, from 100 to 250, from 250 to 500, or any combination of the previous ranges or smaller range therein.

Modifying a zeolite framework by impregnating metal oxides in the framework or by ion exchanging metal atoms into the framework may vary the amount of lattice oxygen present in the zeolite framework, the surface dispersion of the lattice oxygen, and/or the acidity of the catalyst system. The interplay between the lattice oxygen and acidity of the zeolite framework affect the kinetics of the alkane-to-alkene conversion. For example, a catalyst system that is over-acidic or contains excessive lattice oxygen may result in excessive cracking and produce low-value methane and/or carbon oxides. We unexpectedly found that modifying the MFI-type and/or the BEA-type framework with cerium and/or vanadium oxides results in catalyst systems that are kinetically capable of catalyzing both catalytic cracking and dehydrogenation. We also found that the presently disclosed catalyst system has a low selectivity towards methane and/or carbon oxides.

According to embodiments, the MFI-type and/or the BEA-type framework may be modified by impregnating metal oxides in the framework or by ion exchanging metal atoms into the framework. According to embodiments, the metal-substituted zeolite may comprise from 0.5 wt. % to 30 wt. % cerium and/or vanadium atoms based on the total weight of the metal-substituted zeolite. For example, the metal-substituted zeolite may comprise cerium and/or vanadium atoms of from 0.5 wt. % to 10 wt. %, from 10 wt. % to 20 wt. %, from 20 wt. % to 30 wt. % or any combination of the previous ranges or smaller range therein, such as from 0.5 wt. % to 20 wt. %, from 0.5 wt. % to 15 wt. %, from 0.5 wt. % to 12.5 wt. %, from 0.5 wt. % to 7.5 wt. %, from 0.5 wt. % to 5 wt. %, from 0.5 wt. % to 2.5 wt. %, from 1 wt. % to 17.5 wt. %, from 1 wt. % to 15 wt. %, from 1 wt. % to 12.5 wt. %, from 1 wt. % to 10 wt. %, from 1 wt. % to 7.5 wt. %, from 1 wt. % to 5 wt. %, from 1 wt. % to 2.5 wt. %, from 2.5 wt. % to 20 wt. %, from 2.5 wt. % to 17.5 wt. %, from 2.5 wt. % to 15 wt. %, from 2.5 wt. % to 12.5 wt. %, from 2.5 wt. % to 10 wt. %, from 2.5 wt. % to 7.5 wt. %, from 2.5 wt. % to 5 wt. %, from 5 wt. % to 20 wt. %, from 5 wt. % to 17.5 wt. %, from 5 wt. % to 15 wt. %, from 5 wt. % to 12.5 wt. %, from 5 wt. % to 10 wt. %, from 5 wt. % to 7.5 wt. %, from 7.5 wt. % to 20 wt. %, from 7.5 wt. % to 17.5 wt. %, from 7.5 wt. % to 15 wt. %, from 7.5 wt. % to 12.5 wt. %, from 7.5 wt. % to 10 wt. %, from 10 wt. % to 20 wt. %, from 10 wt. % to 17.5 wt. %, from 10 wt. % to 15 wt. %, from 10 wt. % to 12.5 wt. %, from 12.5 wt. % to 20 wt. %, from 12.5 wt. % to 17.5 wt. %, from 12.5 wt. % to 15 wt. %, from 15 wt. % to 20 wt. %, from 15 wt. % to 17.5 wt. %, or from 17.5 wt. % to 20 wt. %, based on the total weight of the metal-substituted zeolite.

In some embodiments, the metal-substituted zeolites may comprise from 0.5 wt. % to 20 wt. % cerium atoms, as calculated on a cerium oxide basis, based on the total weight of the metal-substituted zeolites. For example, the metal-substituted zeolite may comprise cerium atoms of 0.5 wt. % to 5 wt. %, from 5 wt. % to 10 wt. %, from 10 wt. % to 15 wt. %, from 15 wt. % to 20 wt. %, or any combination of the previous ranges or smaller range therein, such as from 5 wt. % to 20 wt. %, from 5 wt. % to 17.5 wt. %, from 5 wt. % to 15 wt. %, from 5 wt. % to 12.5 wt. %, from 5 wt. % to 7.5 wt. %, from 7.5 wt. % to 20 wt. %, from 7.5 wt. % to 17.5 wt. %, from 7.5 wt. % to 15 wt. %, from 7.5 wt. % to 12.5 wt. %, from 7.5 wt. % to 10 wt. %, from 10 wt. % to 20 wt. %, from 10 wt. % to 17.5 wt. %, from 10 wt. % to 12.5 wt. %, from 12.5 wt. % to 20 wt. %, from 12.5 wt. % to 17.5 wt. %, from 12.5 wt. % to 15 wt. %, from 15 wt. % to 17.5 wt. %, or from 17.5 wt. % to 20 wt. %, based on the total weight of the metal-substituted zeolite.

In some embodiments, the metal-substituted zeolites may comprise from 0.5 wt. % to 10 wt. % vanadium atoms, as calculated on a vanadium oxide basis, based on the total weight of the metal-substituted zeolites. In embodiments, the metal-substituted zeolite may comprise vanadium atoms of from 0.5 wt. % to 5 wt. %, from 5 wt. % to 10 wt. % or any combination of the previous ranges or smaller range therein, such as from 1 wt. % to 7.5 wt. %, from 1 wt. % to 6.5 wt. %, from 1 wt. % to 5.5 wt. %, from 1 wt. % to 4.5 wt. %, from 1 wt. % to 3.5 wt. %, from 1 wt. % to 2.5 wt. %, from 1.5 wt. % to 7.5 wt. %, from 1.5 wt. % to 6.5 wt. %, from 1.5 wt. % to 5.5 wt. %, from 1.5 wt. % to 4.5 wt. %, from 1.5 wt. % to 3.5 wt. %, from 1.5 wt. % to 2.5 wt. %, from 2.5 wt. % to 7.5 wt. %, from 2.5 wt. % to 6.5 wt. %, from 2.5 wt. % to 5.5 wt. %, from 2.5 wt. % to 4.5 wt. %, from 2.5 wt. % to 3.5 wt. %, from 3.5 wt. % to 7.5 wt. %, from 3.5 wt. % to 6.5 wt. %, from 3.5 wt. % to 5.5 wt. %, from 3.5 wt. % to 4.5 wt. %, from 4.5 wt. % to 7.5 wt. %, from 4.5 wt. % to 6.5 wt. %, or from 4.5 wt. % to 5.5 wt. %, based on the total weight of the metal-substituted zeolite.

Optionally, the metal-substituted zeolites comprising cerium and/or vanadium atoms may further comprise at least one additional metal oxide, for example, selected from a group consisting of calcium oxides, strontium oxides, magnesium oxides, molybdenum oxides, and combinations thereof. For example, and in embodiments, the metal-substituted zeolites comprising cerium and/or vanadium atoms may further comprise the at least one additional metal oxide by impregnating metal oxides in the framework or by ion exchanging metal atoms into the framework. In some embodiments, the metal-substituted zeolites comprising cerium and/or vanadium atoms may further comprise the at least one additional metal oxide from 0.5 wt. % to 10 wt. % of the metal-substituted zeolite, such as from 0.5 wt. % to 7.5 wt. %, from 0.5 wt. % to 5 wt. %, from 0.5 wt. % to 4.5 wt. %, from 0.5 wt. % to 4 wt. %, from 0.5 wt. % to 3.5 wt. %, from 0.5 wt. % to 3 wt. %, from 0.5 wt. % to 2.5 wt. %, from 0.5 wt. % to 2 wt. %, from 0.5 wt. % to 1.5 wt. %, from 0.5 wt. % to 1 wt. %, from 1 wt. % to 10 wt. %, from 1 wt. % to 7.5 wt. %, from 1 wt. % to 5 wt. %, from 1 wt. % to 4.5 wt. %, from 1 wt. % to 4 wt. %, from 1 wt. % to 3.5 wt. %, from 1 wt. % to 3 wt. %, from 1 wt. % to 2.5 wt. %, from 1 wt. % to 2 wt. %, from 1 wt. % to 1.5 wt. %, from 1.5 wt. % to 10 wt. %, from 1.5 wt. % to 7.5 wt. %, from 1.5 wt. % to 5 wt. %, from 1.5 wt. % to 4.5 wt. %, from 1.5 wt. % to 4 wt. %, from 1.5 wt. % to 3.5 wt. %, from 1.5 wt. % to 3 wt. %, from 1.5 wt. % to 2.5 wt. %, from 1.5 wt. % to 2 wt. %, from 2 wt. % to 10 wt. %, from 2 wt. % to 7.5 wt. %, from 2 wt. % to 5 wt. %, from 2 wt. % to 4.5 wt. %, from 2 wt. % to 4 wt. %, from 2 wt. % to 3.5 wt. %, from 2 wt. % to 3 wt. %, from 2 wt. % to 2.5 wt. %, from 2.5 wt. % to 10 wt. %, from 2.5 wt. % to 7.5 wt. %, from 2.5 wt. % to 5 wt. %, from 2.5 wt. % to 4.5 wt. %, from 2.5 wt. % to 4 wt. %, from 2.5 wt. % to 3.5 wt. %, from 2.5 wt. % to 3 wt. %, from 3 wt. % to 10 wt. %, from 3 wt. % to 7.5 wt. %, from 3 wt. % to 5 wt. %, from 3 wt. % to 4.5 wt. %, from 3 wt. % to 4 wt. %, from 3 wt. % to 3.5 wt. %, from 3.5 wt. % to 10 wt. %, from 3.5 wt. % to 7.5 wt. %, from 3.5 wt. % to 5 wt. %, from 3.5 wt. % to 4.5 wt. %, from 3.5 wt. % to 4 wt. %, from 4 wt. % to 10 wt. %, from 4 wt. % to 7.5 wt. %, from 4 wt. % to 5 wt. %, from 4 wt. % to 4.5 wt. %, from 4.5 wt. % to 10 wt. %, from 4.5 wt. % to 7.5 wt. %, from 4.5 wt % to 5 wt. %, from 5 wt. % to 10 wt. %, from 5 wt. % to 7.5 wt. %, or from 7.5 wt. % to 10 wt. % of the metal-substituted zeolite.

Optionally, the at least one additional metal atom may be selected from the group consisting of lanthanum, copper, molybdenum, and strontium by ion exchanging into the MFI-type and/or the BEA-type framework. In embodiments, the metal-substituted zeolites may comprise the at least one additional metal atom from 0.5 wt. % to 10 wt. % of the metal-substituted zeolite, such as from 0.5 wt. % to 7.5 wt. %, from 0.5 wt. % to 5 wt. %, from 0.5 wt. % to 4.5 wt. %, from 0.5 wt. % to 4 wt. %, from 0.5 wt. % to 3.5 wt. %, from 0.5 wt. % to 3 wt. %, from 0.5 wt. % to 2.5 wt. %, from 0.5 wt. % to 2 wt. %, from 0.5 wt. % to 1.5 wt. %, from 0.5 wt. % to 1 wt. %, from 1 wt. % to 10 wt. %, from 1 wt. % to 7.5 wt. %, from 1 wt. % to 5 wt. %, from 1 wt. % to 4.5 wt. %, from 1 wt. % to 4 wt. %, from 1 wt. % to 3.5 wt. %, from 1 wt. % to 3 wt. %, from 1 wt. % to 2.5 wt. %, from 1 wt. % to 2 wt. %, from 1 wt. % to 1.5 wt. %, from 1.5 wt. % to 10 wt. %, from 1.5 wt. % to 7.5 wt. %, from 1.5 wt. % to 5 wt. %, from 1.5 wt. % to 4.5 wt. %, from 1.5 wt. % to 4 wt. %, from 1.5 wt. % to 3.5 wt. %, from 1.5 wt. % to 3 wt. %, from 1.5 wt. % to 2.5 wt. %, from 1.5 wt. % to 2 wt. %, from 2 wt. % to 10 wt. %, from 2 wt. % to 7.5 wt. %, from 2 wt. % to 5 wt. %, from 2 wt. % to 4.5 wt. %, from 2 wt. % to 4 wt. %, from 2 wt. % to 3.5 wt. %, from 2 wt. % to 3 wt. %, from 2 wt. % to 2.5 wt. %, from 2.5 wt. % to 10 wt. %, from 2.5 wt. % to 7.5 wt. %, from 2.5 wt. % to 5 wt. %, from 2.5 wt. % to 4.5 wt. %, from 2.5 wt. % to 4 wt. %, from 2.5 wt. % to 3.5 wt. %, from 2.5 wt. % to 3 wt. %, from 3 wt. % to 10 wt. %, from 3 wt. % to 7.5 wt. %, from 3 wt. % to 5 wt. %, from 3 wt. % to 4.5 wt. %, from 3 wt. % to 4 wt. %, from 3 wt. % to 3.5 wt. %, from 3.5 wt. % to 10 wt. %, from 3.5 wt. % to 7.5 wt. %, from 3.5 wt. % to 5 wt. %, from 3.5 wt. % to 4.5 wt. %, from 3.5 wt. % to 4 wt. %, from 4 wt. % to 10 wt. %, from 4 wt. % to 7.5 wt. %, from 4 wt. % to 5 wt. %, from 4 wt. % to 4.5 wt. %, from 4.5 wt. % to 10 wt. %, from 4.5 wt. % to 7.5 wt. %, from 4.5 wt % to 5 wt. %, from 5 wt. % to 10 wt. %, from 5 wt. % to 7.5 wt. %, or from 7.5 wt. % to 10 wt. % of the metal-substituted zeolite.

References will now be made in detail to embodiments of methods of converting natural gasoline liquid (NGL) feed to light olefins using the catalyst systems described hereinabove.

According to embodiments, methods of converting NGL feed to light olefins may comprise contacting the NGL feed comprising alkanes with the catalyst systems described hereinabove in a reactor system, thereby converting a portion of the NGL feed to light olefins and yielding a product stream comprising the light olefins. In some embodiments, the reactor system may be substantially free of a gaseous oxidant. As used herein, "substantial absence of a gaseous oxidant" or "substantially free of a gaseous oxidant" means the presence of the gaseous oxidant in the NGL feed or the reactor system may be less than or equal to 1 wt. %, such as less than or equal to 0.5 wt. % or less than or equal to 0.01 wt. %.

Regarding the NGL feed, in one or more embodiments, the NGL feed may comprise greater than or equal to 80 wt. % and less than or equal to 99 wt. % the alkanes, such as greater than or equal to 80 wt. % and less than or equal to 95 wt. %, greater than or equal to 80 wt. % and less than or equal to 90 wt. %, greater than or equal to 80 wt. % and less than or equal to 85 wt. %, greater than or equal to 85 wt. % and less than or equal to 99 wt. %, greater than or equal to 85 wt. % and less than or equal to 95 wt. %, greater than or equal to 85 wt. % and less than or equal to 90 wt. %, greater than or equal to 90 wt. % and less than or equal to 99 wt. %, or greater than or equal to 90 wt. % and less than or equal to 95 wt. %.

In some embodiments, the NGL feed may comprise a boiling point greater than or equal to 25° C. and less than or equal to 250° C., such as greater than or equal to 25° C. and less than or equal to 225° C., greater than or equal to 25° C. and less than or equal to 200° C., greater than or equal to 25° C. and less than or equal to 180° C., greater than or equal to 25° C. and less than or equal to 150° C., greater than or equal to 25° C. and less than or equal to 120° C., or greater than or equal to 25° C. and less than or equal to 75° C. In some embodiments, the NGL feed may comprise a boiling point greater than or equal to 75° C. and less than or equal to 250° C., such as greater than or equal to 75° C. and less than or equal to 225° C., greater than or equal to 75° C. and less than or equal to 200° C., greater than or equal to 75° C. and less than or equal to 180° C., greater than or equal to 75° C. and less than or equal to 150° C., or greater than or equal to 75° C. and less than or equal to 120° C. In some embodiments, the NGL feed may comprise a boiling point greater than or equal to 120° C. and less than or equal to 250° C., such as greater than or equal to 120° C. and less than or equal to 225° C., greater than or equal to 120° C. and less than or equal to 200° C., greater than or equal to 120° C. and less than or equal to 180° C., or greater than or equal to 120° C. and less than or equal to 150° C. In some embodiments, the NGL feed may comprise a boiling point greater than or equal to 150° C. and less than or equal to 250° C., such as greater than or equal to 150° C. and less than or equal to 225° C., greater than or equal to 150° C. and less than or equal to 200° C., or greater than or equal to 150° C. and less than or equal to 180° C. In some embodiments, the NGL feed may comprise a boiling point greater than or equal to 180° C. and less than or equal to 250° C., such as greater than or equal to 180° C. and less than or equal to 225° C., greater than or equal to 180° C. and less than or equal to 200° C., greater than or equal to 200° C. and less than or equal to 250° C., ° C., greater than or equal to 200° C. and less than or equal to 225° C., or greater than or equal to 225° C. and less than or equal to 250° C.

In some embodiments, the alkanes may comprise from 40 wt. % to 95 wt. % light alkanes having less than or equal to six carbons (C1-C6 alkanes), such as from 40 wt. % to 90 wt. %, from 40 wt. % to 80 wt. %, from 40 wt. % to 70 wt. %, from 40 wt. % to 60 wt. %, from 40 wt. % to 50 wt. %, from 50 wt. % to 95 wt. %, from 50 wt. % to 90 wt. %, from 50 wt. % to 80 wt. %, from 50 wt. % to 70 wt. %, from 50 wt. % to 60 wt. %, from 60 wt. % to 95 wt. %, from 60 wt. % to 90 wt. %, from 60 wt. % to 80 wt. %, from 60 wt. % to 70 wt. %, from 70 wt. % to 95 wt. %, from 70 wt. % to 90 wt. %, from 70 wt. % to 80 wt. %, or from 80 wt. % to 95 wt. % light alkanes having less than or equal to six carbons.

In some embodiments, the alkanes may comprise from 0 wt. % to 10 wt. % light alkanes having less than or equal to four carbons (C1-C4 alkanes), such as from 0 wt. % to 5 wt. %, from 0 wt. % to 2 wt. %, from 0 wt. % to 1 wt. %, from 1 wt. % to 10 wt. %, from 1 wt. % to 5 wt. %, from 1 wt. % to 2 wt. %, from 2 wt. % to 10 wt. %, from 2 wt. % to 5 wt. %, or from 5 wt. % to 10 wt. % light alkanes having less than or equal to four carbons.

Regarding the reactor, as used herein, "reactor" refers to any vessel, container, conduit, or the like, in which a chemical reaction occurs. Example reactors include packed bed reactors such as fixed bed reactors, ebullated-bed reactors, moving-bed reactors, and fluidized bed reactors. According to embodiments, the reactor system may comprise a fluidized bed reactor, a fixed bed reactor, or combinations thereof.

In some embodiments, the NGL feed may contact with the catalyst system in the fluidized bed reactor at a temperature of from 400° C. to 650° C., such as from 400° C. to 600° C., from 400° C. to 550° C., from 400° C. to 500° C., from 400° C. to 450° C., from 450° C. to 650° C., from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C.

In some embodiments, the NGL feed may contact with the catalyst system in the fluidized bed reactor under a pressure of from 0.1 bar to 2.5 bar, such as from 0.1 bar to 2 bar, from 0.1 bar to 1.5 bar, from 0.1 bar from 1 bar, from 0.1 bar to 0.5 bar, from 0.5 bar to 2.5 bar, from 0.5 bar to 2 bar, from 0.5 bar to 1.5 bar, from 0.5 bar from 1 bar, from 1 bar to 2.5 bar, from 1 bar to 2 bar, from 1 bar to 1.5 bar, from 1.5 bar to 2.5 bar, from 1.5 bar to 2 bar, or from 2 bar to 2.5 bar.

In one or more embodiments, wherein the reactor system comprises a fluidized bed reactor, the NGL feed may enter the reactor system and contact with the catalyst system in the fluidized bed reactor at a temperature of from 400° C. to 650° C., and a pressure of from 0.1 bar to 2.5 bar.

Further, in some embodiments, the NGL feed may enter the reactor system and contact with the catalyst system at a catalyst-to-feed ratio of from 1 to 20, such as from 1 to 15, from 1 to 12, from 1 to 10, from 1 to 7.5, from 1 to 5, from 1 to 2.5, from 2.5 to 20, from 2.5 to 15, from 2.5 to 12, from 2.5 to 10, from 2.5 to 7.5, from 2.5 to 5, from 5 to 20, from 5 to 15, from 5 to 12, from 5 to 10, from 5 to 7.5, from 7.5 to 20, from 7.5 to 15, from 7.5 to 12, from 7.5 to 10, from 10 to 20, from 10 to 15, from 10 to 12, from 12 to 20, from 12 to 15, or from 15 to 20.

Regarding the conversion of the NGL feed to light olefins, we unexpectedly observed that the catalyst systems disclosed hereinabove demonstrate a high selectivity towards light olefins having less than or equal to four carbons (C2-C4 olefines). In some embodiments, the catalyst system may have a selectivity towards C2-C4 olefines of from 30 wt. % to 70 wt. % based on the total weight of the product stream, such as from 30 wt. % to 65 wt. %, from 30 wt. % to 60 wt. % from 30 wt. % to 55 wt. % from 30 wt. % to 50 wt. %, from 30 wt. % to 45 wt. %, from 30 wt. % to 40 wt. %, from 30 wt. % to 35 wt. %, from 35 wt. % to 70 wt., from 35 wt. % to 65 wt. %, from 35 wt. % to 60 wt. %, from 35 wt. % to 55 wt. %, from 35 wt. % to 50 wt. %, from 35 wt. % to 45 wt. %, from 35 wt. % to 40 wt. %, from 40 wt. % to 70 wt. %, from 40 wt. % to 65 wt. %, from 40 wt. % to 60 wt. %, from 40 wt. % to 55 wt. %, from 40 wt. % to 50 wt. %, from 40 wt. % to 45 wt. %, from 45 wt. % to 70 wt. %, from 45 wt. % to 65 wt. %, from 45 wt. % to 60 wt. %, from 45 wt. % to 55 wt. %, from 45 wt. % to 50 wt. %, from 50 wt. % to 70 wt. %, from 50 wt. % to 65 wt. %, from 50 wt. % to 60 wt. %, from 50 wt. % to 55 wt. %, from 55 wt. % to 70 wt. %, from 55 wt. % to 65 wt. %, from 55 wt. % to 60 wt. %, from 60 wt. % to 70 wt. %, from 60 wt. % to 65 wt. %, or from 65 wt. % to 70 wt. %, based on the total weight of the product stream.

Therefore, according to embodiments, the product stream may comprise the light olefins of from 40 wt. % to 70 wt. % based on the total weight of the product stream, such as from 40 wt. % to 65 wt. %, from 40 wt. % to 60 wt. %, from 40 wt. % to 55 wt. %, from 40 wt. % to 50 wt. %, from 40 wt. % to 45 wt. %, from 45 wt. % to 70 wt. %, from 45 wt. % to 65 wt. %, from 45 wt. % to 60 wt. %, from 45 wt. % to 55 wt. %, from 45 wt. % to 50 wt. %, from 50 wt. % to 70 wt. %, from 50 wt. % to 65 wt. %, from 50 wt. % to 60 wt. %, from 50 wt. % to 55 wt. %, from 55 wt. % to 70 wt. %, from 55 wt. % to 65 wt. %, from 55 wt. % to 60 wt. %, from 60 wt. % to 70 wt. %, from 60 wt. % to 65 wt. %, or from 65 wt. % to 70 wt. %, based on the total weight of the product stream.

Among the light olefins, the catalyst systems demonstrate a relatively high selectivity towards to butenes. In some embodiments, the catalyst system may comprise a selectivity towards butenes of from 20 wt. % to 80 wt. % based on the total weight of the light olefins, such as from 20 wt. % to 75 wt. %, from 20 wt. % to 70 wt. %, from 20 wt. % to 65 wt. %, from 20 wt. % to 60 wt. %, from 20 wt. % to 55 wt. %, from 20 wt. % to 50 wt. %, from 20 wt. % to 45 wt. %, from 20 wt. % to 40 wt. %, from 20 wt. % to 35 wt. %, from 20 wt. % to 30 wt. %, from 20 wt. % to 25 wt. %, from 25 wt. % to 80 wt. %, from 25 wt. % to 75 wt. %, from 25 wt. % to 70 wt. %, from 25 wt. % to 65 wt. %, from 25 wt. % to 60 wt. %, from 25 wt. % to 55 wt. %, from 25 wt. % to 50 wt. %, from 25 wt. % to 45 wt. %, from 25 wt. % to 40 wt. %, from 25 wt. % to 35 wt. %, from 25 wt. % to 30 wt. %, from 30 wt. % to 80 wt. %, from 30 wt. % to 75 wt. %, from 30 wt. % to 70 wt. %, from 30 wt. % to 65 wt. %, from 30 wt. % to 60 wt. %, from 30 wt. % to 55 wt. %, from 30 wt. % to 50 wt. %, from 30 wt. % to 45 wt. %, from 30 wt. % to 40 wt. %, from 30 wt. % to 35 wt. %, from 35 wt. % to 80 wt. %, from 35 wt. % to 75 wt. %, from 35 wt. % to 70 wt. %, from 35 wt. % to 65 wt. %, from 35 wt. % to 60 wt. %, from 35 wt. % to 55 wt. %, from 35 wt. % to 50 wt. %, from 35 wt. % to 45 wt. %, from 35 wt. % to 40 wt. %, from 40 wt. % to 80 wt. %, from 40 wt. % to 75 wt. %, from 40 wt. % to 70 wt. %, from 40 wt. % to 65 wt. %, from 40 wt. % to 60 wt. %, from 40 wt. % to 55 wt. %, from 40 wt. % to 50 wt. %, from 40 wt. % to 45 wt. %, from 45 wt. % to 80 wt. %, from 45 wt. % to 75 wt. %, from 45 wt. % to 70 wt. %, from 45 wt. % to 65 wt. %, from 45 wt. % to 60 wt. %, from 45 wt. % to 55 wt. %, from 45 wt. % to 50 wt. %, from 50 wt. % to 80 wt. %, from 50 wt. % to 75 wt. %, from 50 wt. % to 70 wt. %, from 50 wt. % to 65 wt. %, from 50 wt. % to 60 wt. %, from 50 wt. % to 55 wt. %, from 55 wt. % to 80 wt. %, from 50 wt. % to 75 wt. %, from 55 wt. % to 70 wt. %, from 55 wt. % to 65 wt. %, from 55 wt. % to 60 wt. %, from 60 wt. % to 80 wt. %, from 60 wt. % to 75 wt. %, from 60 wt. % to 70 wt. %, from 60 wt. % to 65 wt. %, from 65 wt. % to 80 wt. %, from 65 wt. % to 75 wt. %, from 65 wt. % to 70 wt. %, from 70 wt. % to 80 wt. %, from 70 wt. % 75 wt. %, or from 75 wt. % to 80 wt. % based on the total weight of the light olefins.

In some embodiments, the catalyst system may have a selectivity towards butenes of from 10 wt. % to 50 wt. % based on the total weight of the product stream, such as from 10 wt. % to 45 wt. %, from 10 wt. % to 40 wt. %, from 10 wt. % to 35 wt. %, from 10 wt. % to 30 wt. %, from 10 wt. % to 25 wt. %, from 10 wt. % to 20 wt. %, from 15 wt. % to 50 wt. %, from 15 wt. % to 45 wt. %, from 15 wt. % to 40 wt. %, from 15 wt. % to 35 wt. %, from 15 wt. % to 30 wt. %, from 15 wt. % to 25 wt. %, from 15 wt. % to 20 wt. %, from 20 wt. % to 50 wt. %, from 20 wt. % to 45 wt. %, from 20 wt. % to 40 wt. %, from 20 wt. % to 35 wt. %, from 20 wt. % to 30 wt. %, from 20 wt. % to 25 wt. %, from 25 wt. % to 50 wt. %, from 25 wt. % to 45 wt. %, from 25 wt.

% to 40 wt. %, from 25 wt. % to 35 wt. %, from 25 wt. % to 30 wt. %, from 30 wt. % to 50 wt. %, from 30 wt. % to 45 wt. %, from 30 wt. % to 40 wt. %, from 30 wt. % to 35 wt. %, from 35 wt. % to 50 wt. %, from 35 wt. % to 45 wt. %, from 35 wt. % to 40 wt. %, from 40 wt. % to 50 wt. %, from 40 wt. % to 45 wt. %, or from 45 wt. % to 50 wt. % based on the total weight of the product stream.

Therefore, in some embodiments, the product stream may comprise butenes of from 5 wt. % to 50 wt. % based on the total weight of the product stream, such as from 5 wt. % to 45 wt. %, from 5 wt. % to 40 wt. %, from 5 wt. % to 35 wt. %, from 5 wt. % to 30 wt. %, from 5 wt. % to 25 wt. %, from 5 wt. % to 20 wt. %, from 5 wt. % to 10 wt. %, from 10 wt. % to 50 wt. %, from 10 wt. % to 45 wt. %, from 10 wt. % to 40 wt. %, from 10 wt. % to 35 wt. %, from 10 wt. % to 30 wt. %, from 10 wt. % to 25 wt. %, from 10 wt. % to 20 wt. %, from 20 wt. % to 50 wt. %, from 20 wt. % to 45 wt. %, from 20 wt. % to 40 wt. %, from 20 wt. % to 35 wt. %, from 20 wt. % to 30 wt. %, from 20 wt. % to 25 wt. %, from 25 wt. % to 50 wt. %, from 25 wt. % to 45 wt. %, from 25 wt. % to 40 wt. %, from 25 wt. % to 35 wt. %, from 25 wt. % to 30 wt. %, from 30 wt. % to 50 wt. %, from 30 wt. % to 45 wt. %, from 30 wt. % to 40 wt. %, from 30 wt. % to 35 wt. %, from 35 wt. % to 50 wt. %, from 35 wt. % to 45 wt. %, from 35 wt. % to 40 wt. %, from 40 wt. % to 50 wt. %, from 40 wt. % to 45 wt. %, or from 45 wt. % to 50 wt. %, based on the total weight of the product stream.

Surprisingly, and in embodiments, the catalyst systems demonstrate a low selectivity towards methane and $CO_x$, wherein the $CO_x$ consists of CO, $CO_2$, and a combination thereof.

In some embodiments, the catalyst systems may have a selectivity towards $CO_x$ less than 10 wt. %, based on the total weight of the product stream, such as less than or equal to 8 wt. %, less than or equal to 6 wt. %, less than or equal to 4 wt. %, less than or equal to 2 wt. %, less than or equal to 1 wt. %, from greater than or equal to 1 wt. % to less than 10 wt. %, from greater than or equal to 1 wt. % to less than or equal to 8 wt. %, from greater than or equal to 1 wt. % to less than or equal to 6 wt. %, from greater than or equal to 1 wt. % to less than or equal to 4 wt. %, from greater than or equal to 1 wt. % to less than or equal to 2 wt. %, from greater than or equal to 2 wt. % to less than 10 wt. %, from greater than or equal to 2 wt. % to less than or equal to 8 wt. %, from greater than or equal to 2 wt. % to less than or equal to 6 wt. %, from greater than or equal to 2 wt. % to less than or equal to 4 wt. %, from greater than or equal to 4 wt. % to less than 10 wt. %, from greater than or equal to 4 wt. % to less than or equal to 8 wt. %, from greater than or equal to 4 wt. % to less than or equal to 6 wt. %, from greater than or equal to 6 wt. % to less than 10 wt. %, from greater than or equal to 6 wt. % to less than or equal to 8 wt. %, or from greater than or equal to 8 wt. % to less than 10 wt. %, based on the total weight of the product stream. Due to the low selectivity towards to $CO_x$, in some embodiments, the product streams may comprise substantially free of $CO_x$. As used herein, "substantially free of $CO_x$" means the presence of the $CO_x$ in the product stream may be less than or equal to 1 wt. %, such as less than or equal to 0.5 wt. % or less than or equal to 0.01 wt. %.

In other embodiments, the catalyst systems may have a selectivity towards methane less than or equal to 5 wt. %, based on the total weight of the product stream, such as less than 4 wt. %, less than 3 wt. %, greater than or equal to 2 wt. % and less than or equal to 5 wt. %, greater than or equal to 3 wt. % and less than or equal to 5 wt. %, greater than or equal to 3 wt. % and less than or equal to 4 wt. %, or greater than or equal to 4 wt. % and less than or equal to 5 wt. %.

Upon converting the NGL feed to olefins, the lattice oxygen may be released from the catalyst systems during the conversion process. The spent catalyst system may therefore comprise a lower catalytic strength or become inactive. The spent catalyst system may recover the lost lattice oxygen by a regeneration process, in which the spent catalyst system may be contacted by a regeneration feed comprising a gaseous oxidant or air and for a regenerated catalyst system.

According to embodiments, methods of converting NGL feed to light olefins may further comprise introducing a spent catalyst system into a regenerator of the reactor system; contacting the spent catalyst system with a regeneration feed comprising a gaseous oxidant in a regenerating reactor system, and thereby regenerating a portion of the spent catalyst system and forming a regenerated catalyst system.

In some embodiments, the regenerator may comprise a temperature of from 550° C. to 750° C., such as from 550° C. to 700° C., from 550° C. to 650° C., from 550° C. to 600° C., from 600° C. to 750° C., from 600° C. to 700° C., from 600° C. to 650° C., from 650° C. to 750° C., from 650° C. to 700° C., or from 700° C. to 750° C.

In other embodiments, the regenerator may comprise a pressure of from 0.1 bar to 2.0 bar, such as from 0.1 bar to 1.5 bar, from 0.1 bar to 1.0 bar, from 0.1 bar to 0.5 bar, from 0.5 bar to 2.0 bar, from 0.5 bar to 1.5 bar, from 0.5 bar to 1.0 bar, from 1.0 bar to 2.0 bar, from 1.0 bar to 1.5 bar, or from 1.5 bar to 2.0 bar.

In some embodiments, the regenerator may comprise a temperature of from 550° C. to 750° C. and a pressure of from 0.1 bar to 2.0 bar.

In other embodiments, the regeneration feed may comprise from 1 wt. % to 25 wt. % the gaseous oxidant, such as from 1 wt. % to 20 wt. %, from 1 wt. % to 10 wt. %, from 1 wt. % to from 1 wt. % to 8 wt. %, from 1 wt. % to 6 wt. % from 1 wt. % to 4 wt. %, from 1 wt. % to 2 wt. %, from 2 wt. % to 25 wt. %, from 2 wt. % to 10 wt. %, from 2 wt. % to 8 wt. %, from 2 wt. % to 6 wt. %, from 2 wt. % to 4 wt. %, from 4 wt. % to 25 wt. %, from 4 wt. % to 10 wt. %, from 4 wt. % to 8 wt. %, from 4 wt. % to 6 wt. %, from 6 wt. % to 25 wt. %, from 6 wt. % to 10 wt. %, from 6 wt. % to 8 wt. %, from 8 wt. % to 25 wt. %, from 8 wt. % to 10 wt. %, or from 10 wt. % to 25 wt. %. In further embodiments, the regeneration feed may be air.

Regarding the regenerator, in one or more embodiments, the reactor system may further comprise the regenerator. In other embodiments, the regenerator may be separated from the reactor system.

EXAMPLES

The various embodiments of catalyst systems and methods for converting natural gasoline liquid will be further clarified by the following examples. The examples are illustrative in nature, and should not be understood to limit the subject matter of the present disclosure.

The exemplary catalysts and methods of preparing the same are now described.

Example 1 (E1): ZSM-5 Zeolite Impregnated With 2.5 wt. % Vanadium Oxides (2.5 wt. % VON/ZSM-5)

For Example 1, the catalyst system comprised vanadium oxides ($VO_x$) impregnated in the ZSM-5 framework. The ZSM-5 zeolite component had a silica to alumina mole ratio of 38. $VO_x$/ZSM-5 of Example 1 comprised 2.5 wt. % of $VO_x$ (hereinafter "2.5 wt. % $VO_x$/ZSM-5"), based on the total weight of the metal-substituted zeolite. $VO_x$ was impregnated in the ZSM-5 zeolite framework by wet impregnation methods generally known by a person of ordinary skilled in the art.

Example 2 (E2): ZSM-5 Zeolite Impregnated With 5.0 wt. % Vanadium Oxides (5.0 wt. % $VO_x$/ZSM-5)

For Example 2, the catalyst system comprised 5.0 wt. % vanadium oxides impregnated in the ZSM-5 framework (hereinafter, "5.0 wt. % $VO_x$/ZSM-5"). The 5.0 wt. % $VO_x$/ZSM-5 of Example 2 was prepared according to the method described in Example 1.

Example 3 (E3): Beta Zeolite Ion Exchanged with Cerium (Ce-Beta)

For Example 3, the catalyst system catalyst comprised Beta zeolite with cerium ion exchanged into the Beta framework (hereinafter "Ce-Beta"). The Beta zeolite component had a silica to alumina mole ratio of 360. The Beta zeolite was ion-exchanged with 0.1 M Cerium Nitrate by methods generally known by a person of ordinary skilled in art. The content of Ce atoms in Ce-Beta is estimated to be 5 wt. % to 20 wt. %.

Comparative Example 4 (CE4): Unmodified ZSM-5 Zeolite

For Comparative Example 4, the catalyst system comprised unmodified ZSM-5 zeolite. The ZSM-5 zeolite had a silica to alumina mole ratio of 38.

The performance of the exemplary catalyst system and the condition of testing the catalytic performance are now described. Example 5 describes a catalytic performance test in a fixed bed reactor, and Example 6 describes a catalytic performance test in a fluidized bed reactor. For both Example 5 and Example 6, the catalytic performance was tested in the substantial absence of oxygen in NGL feed and in the reactor. Example 7 describes the result of catalytic performance test in the fixed bed reactor and in the fluidized bed reactor.

Example 5: Catalytic Performance in a Fixed Bed Reactor

In Example 5, the performance of the catalyst system comprising metal-substituted zeolites (Examples 1 to 3) for converting natural gasoline liquid in a fixed bed reactor was compared to the performance of the comparative catalyst (unmodified ZSM-5) for converting the same natural gasoline liquid. The evaluation of each catalyst was conducted in a fixed-bed Micro Activity Test (MAT) unit (Sakuragi Rikagaku, Japan), using a quartz tubular reactor (I.D. 22 mm, and 38 cm in length).

Generally, the MAT unit was conditioned according to ASTM D-3907. For purpose of this disclosure, the MAT unit was modified to include a low temperature circulating bath at −10° C. instead of the conventional iced water considering the high volatility of natural gasoline liquid. Specifically, the MAT unit comprised a reactor-injector assembly including an injector clamed to a reactor containing a catalyst system. The reactor-injector assembly was placed in a heating zone and purged with $N_2$ flow at 30 mL/min for about 15 minutes.

Before injecting NGL feed, a liquid receiver with a product vial was connected to the bottom of the reactor and immersed in the low-temperature bath. The liquid receiver had a gas outlet connected to a burette for gas collection. The MAT unit was purged again for another 15 minutes before injecting NGL feed to initiate a reaction. For all catalyst systems, the test conditions are included in Table 2.

After the reaction was completed, the catalyst system was stripped for 5 minutes using 30 mL/min of $N_2$ flow, and the liquid product was removed from the low-temperature bath and stripped for 3 minutes to remove the gaseous product dissolved in the liquid product. During the reaction and stripping modes, gaseous products were collected in a gas burette by water displacement. Weight of the feed syringe was determined before and after the experiment to obtain the exact weight of oil fed. MAT operating conditions are summarized in Table 1.

TABLE 1

| MAT operating conditions. | |
|---|---|
| Feed weight injected | About 0.9 g |
| Catalyst weight | A multiple of the feed weight to achieve the required catalyst to oil ratio (C/O) |
| Feed injection time (Time on stream) | 30 s |
| Feed syringe temperature | Room temperature |
| Feed injector temperature | 5° C. higher than reaction temperature |
| Liquid receiver temperature | −9° C. |
| Catalyst/liquid stripping time | Total 8 mins |
| with receiver in cold bath | 5 mins |
| with cold bath removed | 3 mins |

Example 6: Catalytic Performance in a Fluidized Bed Reactor

In Example 6, the performance of the catalyst system comprising metal-substituted zeolites (Examples 1 to 3) for converting natural gasoline liquid in a fluidized bed reactor was compared to the performance of the comparative catalyst (unmodified ZSM-5) for converting the same natural gasoline liquid.

The evaluation of each catalyst was conducted in an Advanced Cracking Evaluation (ACE) (Model R+) unit that simulates commercial fluidized catalytic cracking (FCC) units. The ACE unit employed a cyclic operation process, in which vacuum gas oil (VGO) feed, nitrogen, and air were sequentially supplied during well-defined steps of the FCC cycle, to simulate commercial fluidized catalytic cracking (FCC) units that operate with continuous feed and continuous catalyst circulation through several vessels or reactors which comprise the FCC unit.

The laboratory operation was characterized by the following steps: (1) injecting NGL feed over a catalyst system; (2) stripping the catalyst system for a specified duration; and (3) regenerating the catalyst system with air at elevated temperature. For all catalyst systems, the test conditions are included in Table 3.

Before injecting NGL feed, feed pump was calibrated at the feed temperature to deliver specific amount of NGL feed to maintain desired catalyst-to-oil ratio. Specific amounts (6-12 g) of catalyst samples were loaded into the hopper for each experimental run. Liquid receivers were placed in the chilled liquid bath maintained at −15° C.

At the start of operation, the catalyst was transferred to the reactor and heated to the desired reaction temperature with nitrogen gas flew thru the feed injector and from bottom the bottom of the reactor to keep catalyst particles fluidized. When the catalyst bed temperature reached within +1° C. of the reaction temperature, the NGL feed was injected for a preset duration. The entire gaseous product passed thru the liquid received where hydrocarbons comprising five or more carbons were condensed, and non-condensable product passed to a gas receiver.

After the stripping of a catalyst system ended, the reactor temperature was raised to 650° C. and nitrogen was changed to air to regenerate the catalyst system. During the regeneration, the gaseous product was passed thru $CO_2$ analyzer, and total amount of coke produced was calculated from the flue gas flow rate and $CO_2$ concentration.

The hydrocarbon gaseous product was analyzed by the Agilent Micro GC 3000A. The gas from the start of the feed injection to the liquid stripping was collected in a glass bottle by water displacement. The displaced water was collected in a vessel placed on the balance. The difference in the weights of the displaced water before and after gave the volume of the gaseous product.

Example 7: Results of Catalytic Performance

Figure 2:
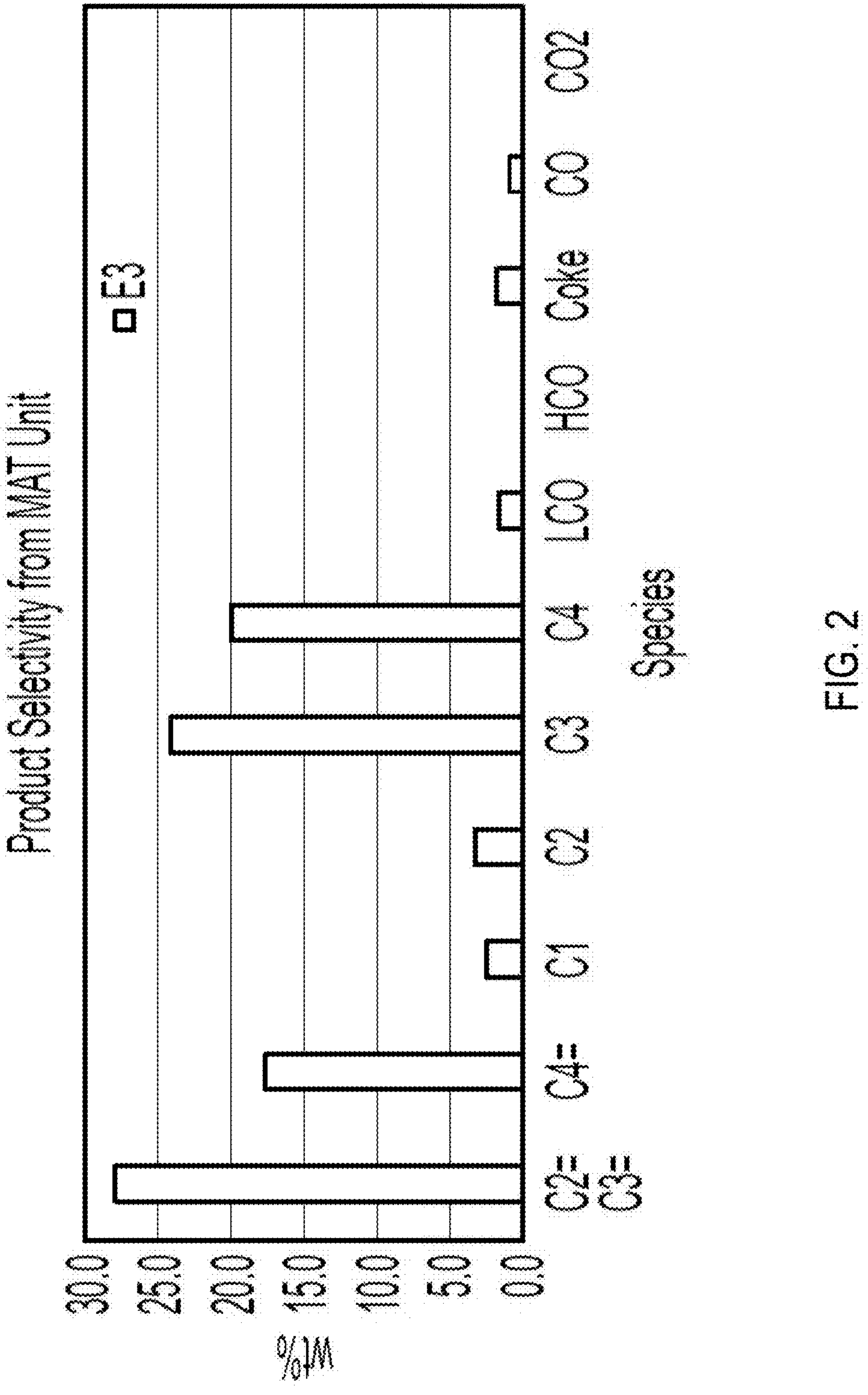
FIG. 2 illustrates product distribution of converting NGL feed to light olefins in the MAT unit using a catalyst system comprising a cerium ion-exchanged Beta zeolite (Ce-Beta)
Figure 3:
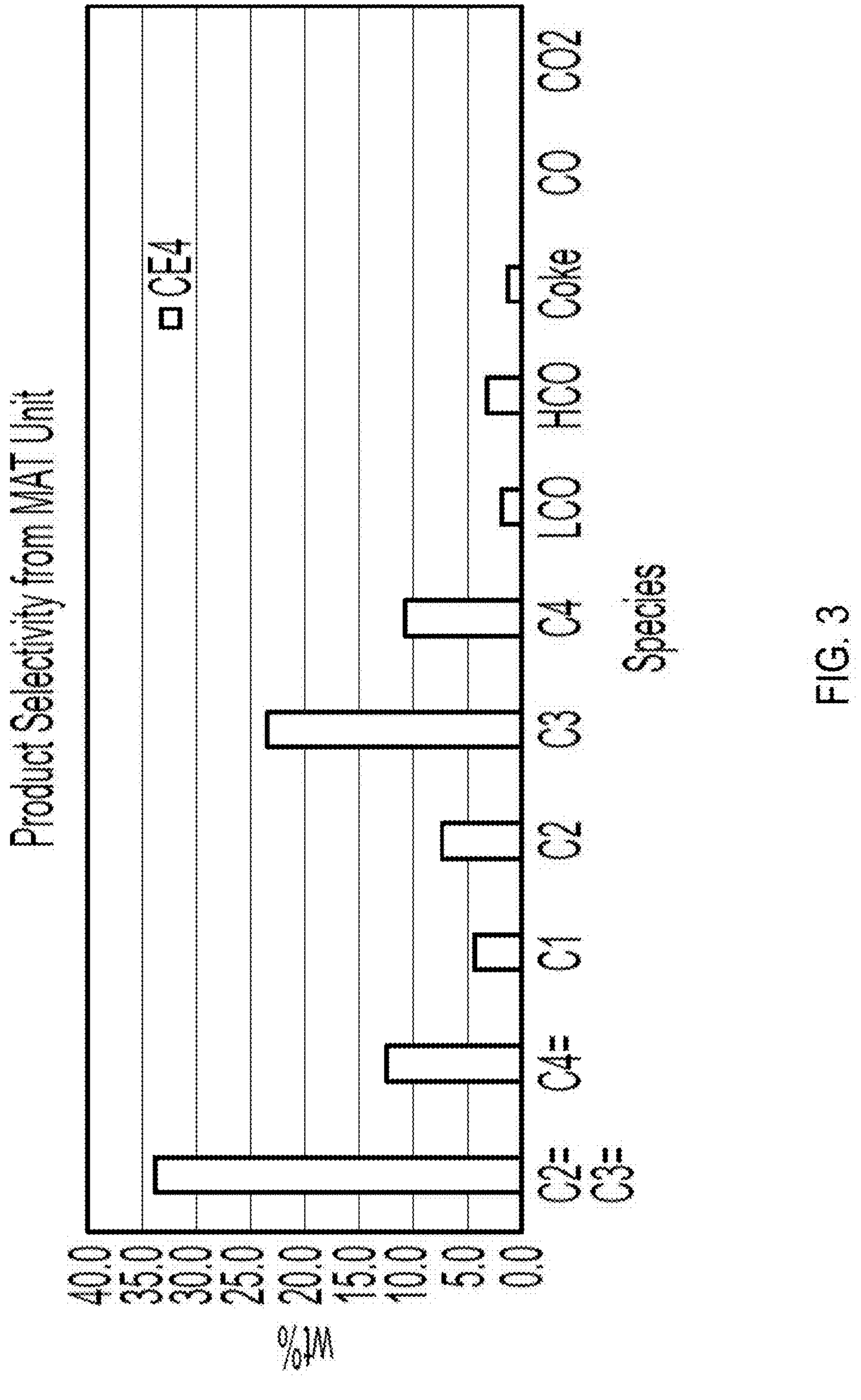
FIG. 3 illustrates product distribution of converting NGL feed to light olefins in the MAT unit using a catalyst system comprising an unmodified ZSM-5 zeolite.
Figure 4:
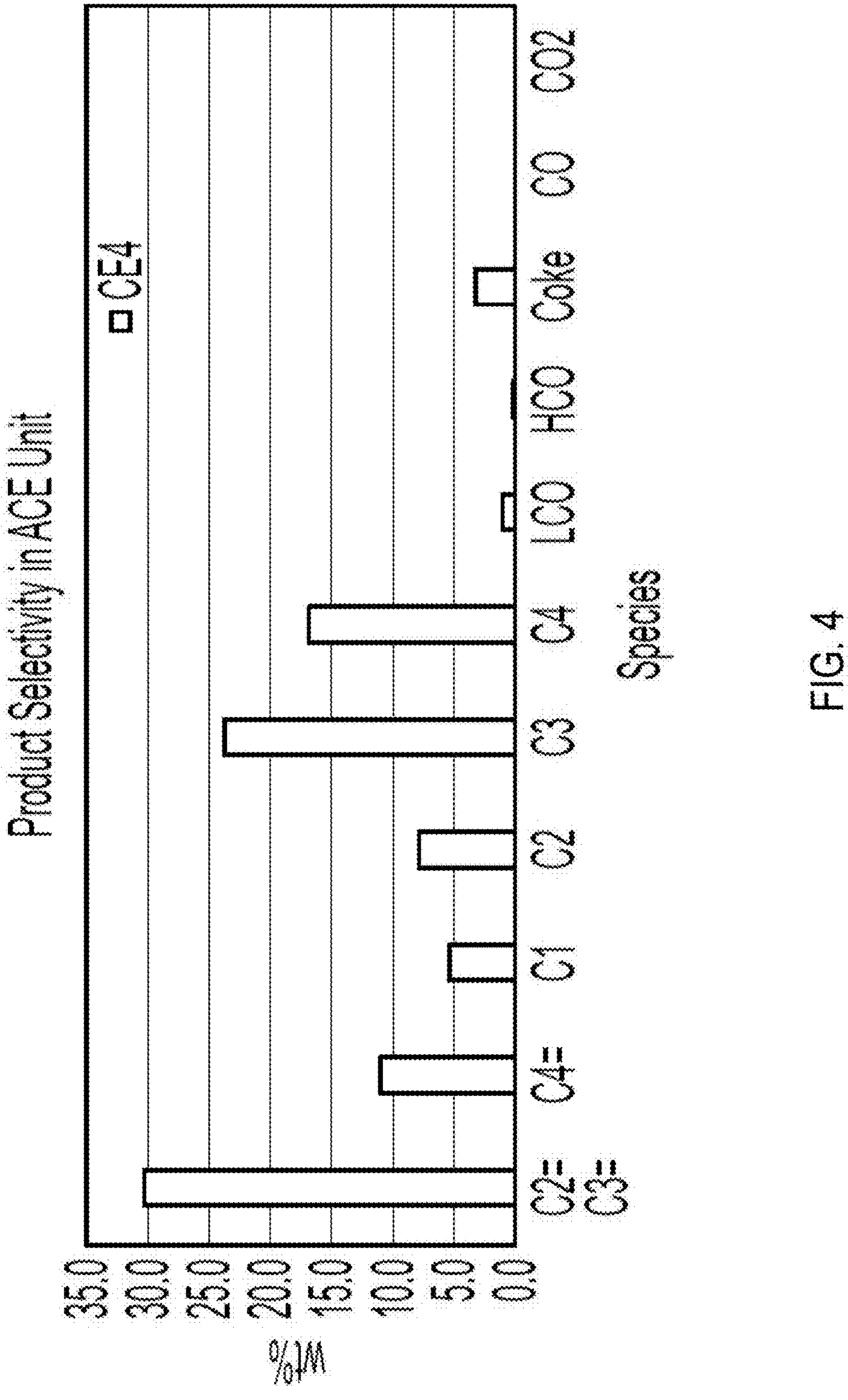
FIG. 4 illustrates product distribution of converting NGL feed to light olefins in the ACE unit using a catalyst system comprising an unmodified ZSM-5 zeolite.

In Example 7, the catalytic performance of Examples 1 to 3 and Comparative Example 4 in the MAT fixed bed unit are summarized in Table 2. The product distribution of converting NGL feed to light olefins in the MAT unit using Example 1, Example 3, and Comparative Example 4 are illustrated in FIGS. 1, 2, and 3, respectively. The catalytic performance of Examples 1 to 3 and Comparative Example 4 in the ACE fluidized bed unit are summarized in Table 3. FIG. 4 illustrates product distribution of converting NGL feed to light olefins in the ACE unit using Comparative Example 4.

TABLE 2

The conversion of NGL to light olefins in the MAT fixed bed reactor.

| Example | E1 2.5 wt. % $VO^x$/ZSM-50 | E2 5.0 wt. % $VO^x$/ZSM-50 | E3 Ce-Beta | CE 4 Unmodified ZSM-50 |
|---|---|---|---|---|
| T.O.S (s) | 20 | 20 | 20 | 20 |
| Catalyst wt (g) | 3.50 | 3.50 | n/a | 3.50 |
| Feed wt (g) | 0.41 | 0.58 | n/a | 0.47 |
| CAT/OIL | 8.62 | 6.08 | 5.89 | 7.40 |
| Temperature (° C.) | 575 | 575 | 575 | 575 |
| Conversion (%) | 31.8 | 43.4 | 52.0 | 58.5 |
| Selectivity (%) | | | | |
| C2 = | 7.9 | 11 | 9 | 13 |
| C3 = | 18.7 | 14 | 19 | 20 |
| C2 = C3 = | 26 | 25 | 28 | 34 |
| C4 = | 23 | 22 | 18 | 13 |
| C1 | 4 | 4 | 3 | 5 |
| C2 | 11 | 7 | 3 | 8 |
| C3 | 19 | 20 | 24 | 24 |
| C4 | 5 | 5 | 20 | 11 |
| LCO | 1 | 0 | 2 | 2 |
| HCO | 0 | 0 | 0 | 3 |
| Coke | 3 | 12 | 2 | 1 |
| CO | 2 | 1 | 1 | 0.0 |
| CO2 | 4 | 4 | 0 | 0.0 |

LCO = light cycle oil
HCO = heavy cycle oil

TABLE 3

The conversion of NGL to light olefins in the ACE fluidized bed reactor.

| Example | E1 2.5 wt. % $VO^x$/ZSM-50 | E2 5.0 wt. % $VO^x$/ZSM-50 | E3 Ce-Beta | CE 4 Unmodified ZSM-50 |
|---|---|---|---|---|
| T.O.S (s) | 30 | 30 | 30 | 30 |
| Catalyst wt (g) | n/a | n/a | n/a | n/a |
| Feed wt (g) | n/a | n/a | n/a | n/a |
| CAT/OIL | 6.40 | 5.93 | 6.32 | 6.40 |
| Temperature (° C.) | 575 | 575 | 575 | 575 |
| Conversion (%) | 36.9 | 31.0 | 45.7 | 40.7 |
| Selectivity (%) | | | | |
| C2 = | 7 | 5 | 10 | 13 |
| C3 = | 13 | 11 | 16 | 18 |
| C2 = C3 = | 20 | 16 | 27 | 30 |
| C4 = | 26 | 35 | 13 | 11 |
| C1 | 4 | 3 | 4 | 5 |
| C2 | 10 | 7 | 5 | 8 |
| C3 | 16 | 10 | 22 | 24 |
| C4 | 5 | 3 | 19 | 17 |
| LCO | 3 | 4 | 1 | 1 |
| HCO | 2 | 7 | 0 | 0 |
| Coke | 8 | 13 | 9 | 3 |
| CO | 0 | 2 | 0 | 0 |
| CO2 | 8 | 1 | 0 | 0 |

LCO = light cycle oil
HCO = heavy cycle oil

As shown in Table 2 and Table 3, the selectivity towards butenes (C4=) of the example catalyst systems (Examples 1 to 3) comprising metal-substituted zeolites was significantly higher than that of an unmodified ZSM-5 (Comparative Example 4) in both the MAT fixed bed reactor and the ACE fluidized bed reactor. Particularly, Examples 1 and 2 ($VO_x$-impregnated ZSM-5 zeolites) showed a twofold and more than threefold increase in the selectivity towards butylenes (C4=) in the MAT fixed bed reactor and the ACE fluidized bed reactor, respectively.

Accordingly, the present disclosure shows the catalyst system comprising a metal-substituted zeolite comprising a MFI-type and/or a BEA-type framework comprising 0.5 wt. % to 30 wt. % cerium and/or vanadium atoms based on the total weight of the catalyst system are capable of catalyzing catalytic cracking and dehydrogenation processes and converting natural gasoline liquid to light olefins with a high selectivity towards butenes. The present disclosure also shows that the use of these catalyst system to convert natural gasoline liquid feed to light olefins with a high selectivity towards butenes of from 20 wt. % to 80 wt. % based on the total weight of the light olefins, and a selectivity towards light olefins having less than or equal to four carbons of from 30 wt. % to 70 wt. % based on the total weight of the product stream.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

What is claimed is:

1. A method of converting natural gasoline liquid (NGL) feed to light olefins comprising:

contacting the NGL feed comprising alkanes with a catalyst system at a temperature range of from 400° C.

to 650° C., and under a pressure range of from 0.1 bar to 2.5 bar, in a fluidized bed reactor, wherein:

the catalyst system comprises a vanadium-substituted zeolite comprising a MFI-type framework, a cerium-substituted zeolite comprising a BEA-type framework, or both, the MFI-type framework comprises vanadium and at least one additional metal oxide, the BEA-type framework comprises cerium and the at least one additional metal oxide, the at least one additional metal oxide is selected from the group consisting of calcium oxide, strontium oxide, magnesium oxide, molybdenum oxide, and combinations thereof, the MFI-type framework comprises from 0.5 wt. % to 30 wt. % vanadium atoms based on a total weight of the vanadium-substituted zeolite, as calculated on a vanadium oxide basis, and the BEA-type framework comprises from 0.5 wt. % to 30 wt. % cerium atoms based on a total weight of the cerium-substituted zeolite, as calculated on a cerium oxide basis, and the MFI-type framework and the BEA-type framework also comprise from 0.5 wt. % to 10 wt. % of the at least one additional metal oxide based on a total weight of the zeolite;

catalyzing catalytic cracking and dehydrogenation of the NGL feed via the catalyst system, thereby converting a portion of the NGL feed to the light olefins and yielding a product stream comprising the light olefins.

2. The method of claim 1, wherein the cerium-substituted zeolite comprises from 0.5 wt. % to 20 wt. % cerium atoms, as calculated on a cerium oxide basis, based on the total weight of the cerium-substituted zeolite.

3. The method of claim 2, wherein the BEA-type framework comprises from 0.5 wt. % to 20 wt. % ion-exchanged cerium atoms.

4. The method of claim 1, wherein the vanadium-substituted zeolite comprises from 0.5 wt. % to 10 wt. % vanadium atoms, as calculated on a vanadium oxide basis, based on the total weight of the vanadium-substituted zeolite.

5. The method of claim 4, wherein the MFI-type framework comprises from 0.5 wt. % to 10 wt. % impregnated vanadium atoms.

6. The method of claim 1, wherein the catalyst system further comprises from 0.5 wt. % to 10 wt. % of at least one additional metal atom selected from the group consisting of lanthanum, copper, molybdenum, strontium or combinations thereof.

7. The method of claim 1, wherein the vanadium-substituted zeolite and the cerium-substituted zeolite comprise a silica-to-alumina molar ratio of from 10 to 500.

8. The method of claim 1, wherein the catalyst system comprises a selectivity towards the light olefins having less than or equal to four carbons of from 30 wt. % to 70 wt. % based on a total weight of the product stream.

9. The method of claim 8, wherein the catalyst system comprises a selectivity towards butenes of from 20 wt. % to 80 wt. % based on a total weight of light olefins.

10. The method of claim 1, wherein the catalyst system comprises a selectivity towards $CO_x$ of less than 10 wt. %, wherein the $CO_x$ consists of CO, $CO_2$, or a combination thereof.

11. The method of claim 1, wherein the catalyst system comprises a selectivity towards methane of less than 5 wt. %.

12. The method of claim 1, wherein the product stream comprises light olefins having less than or equal to four carbons from 40 wt. % to 70 wt. % based on a total weight of the product stream.

13. The method of claim 1, wherein the reactor system is substantially free of a gaseous oxidant.

14. The method of claim 1, wherein the NGL feed contacts with the catalyst system with a catalyst-to-feed ratio of from 1 to 20.

15. The method of claim 1, wherein the NGL feed comprises from 80 wt. % to 99 wt. % alkanes, and wherein the NGL feed comprises a boiling point of from 25° C. to 250° C.

16. The method of claim 1, further comprising introducing a spent catalyst system into a regenerator of the reactor system; contacting the spent catalyst system with a regeneration feed comprising a gaseous oxidant in the regenerator at a temperature of 550° C. to 750° C. and a pressure of from 0.1 bar to 2.0 bar, thereby regenerating a portion of the spent catalyst system and forming a regenerated catalyst system, wherein the gaseous oxidant comprises 1 wt. % to 25 wt. % of the regeneration feed.

17. The method of claim 16, wherein the regeneration feed is air.

* * * * *